United States Patent [19]

Mitchell

[11] Patent Number: 4,602,094
[45] Date of Patent: Jul. 22, 1986

[54] PROCESS FOR PREPARING AMIDOSILANES AND AMIDOSILOXANES

[75] Inventor: Tyrone D. Mitchell, Albany, N.Y.

[73] Assignee: General Electric Company, Waterford, N.Y.

[21] Appl. No.: 772,285

[22] Filed: Sep. 4, 1985

[51] Int. Cl.$^4$ ............................. C07F 7/02; C07F 7/10
[52] U.S. Cl. .................................... 548/406; 556/411; 546/14
[58] Field of Search ....................... 556/411; 548/406; 546/14

[56] References Cited

U.S. PATENT DOCUMENTS

| | | | |
|---|---|---|---|
| 2,876,209 | 3/1959 | de Benneville et al. | 556/411 X |
| 2,876,234 | 3/1959 | Hurwitz et al. | 556/411 X |
| 2,906,756 | 9/1959 | de Benneville et al. | 556/411 X |

*Primary Examiner*—Paul F. Shaver
*Attorney, Agent, or Firm*—Gary L. Loser

[57] ABSTRACT

There is provided a process for preparing amidosilane and amidosiloxanes comprising reacting (1) an Si—H containing compound with (2) an organic amide in the presence of (3) a precious metal containing catalyst.

15 Claims, No Drawings

PROCESS FOR PREPARING AMIDOSILANES AND AMIDOSILOXANES

BACKGROUND OF THE INVENTION

The present invention relates to a novel process for preparing amidosilanes and amidosiloxanes. More particularly, the present invention relates to a process for preparing amidosilanes and amidosiloxanes comprising reacting an organic amide and an Si—H containing compound in the presence of a precious metal containing catalyst.

Precious metal containing hydrosilation catalysts, especially those based on platinum, are well known in the art, for example, as described in U.S. Pat. Nos. 2,823,218; 3,159,601; 3,159,662; 3,220,972; 3,419,593; 3,516,946; 3,814,730; all of which are incorporated by reference into the present disclosure. Generally, these patents teach the addition of an organosilicon material having a hydrogen atom bonded to silicon to an aliphatically unsaturated material having either olefinic or acetylenic unsaturation resulting in the formation of an adduct having a new silicon-carbon linkage. Such reaction can be illustrated with respect to the olefinic bond as follows:

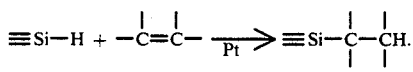

These references, however, do not teach or suggest that the disclosed catalysts are effective for promoting substitution reactions of the type contemplated by the present invention.

de Benneville et al., U.S. Pat. No. 2,876,209, discloses that silicon-containing organic compounds can be prepared by reacting at a temperature of from 10° C. to 180° C., (1) an organic compound consisting of carbon, hydrogen, and at least one atom attached directly to a carbon atom selected from the group consisting of oxygen, sulfur and nitrogen, said compound containing at least one reactive hydrogen atom attached directly to an atom selected from the group consisting of oxygen, sulfur and nitrogen atoms, and (2) a silicon-containing compound having the formula

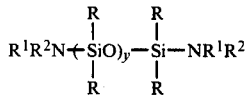

where R is a lower alkyl radical, $R^1$ and $R^2$ are selected from the group consisting of radicals directly attached only to the adjoining nitrogen atom and radicals which together and with the adjoining nitrogen atom form a heterocyclic nucleus, and y is a number of from 1 to about 9. This reaction has the advantage that no catalyst is required, however, it also has the disadvantage that an amine is liberated as a by-product.

Hurwitz et al., U.S. Pat. No. 2,876,234, teaches that aminosilanes of the general formula

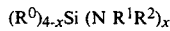

where $R^0$ is cyclohexyl, aryl, alkenyl or alkyl; $R^1$ and $R^2$ together may be the morpholino residue, the piperidino residue or the pyrollidino residue, or separately, $R^1$ may be cyclohexyl, phenyl, aralkyl or alkyl, $R^2$ may be hydrogen, cyclohexyl, aralkyl or alkyl, and x is an integer from 1 to 4; can be reacted with an amide containing a reactive hydrogen to obtain an amidosilane. This process, however, suffers from the disadvantage that large quantities of amine salts are produced as a by-product.

Golitz et al., U.S. Pat. No. 3,417,047, discloses that N-silyl substituted carboxylic acid amides can be obtained by reacting a halosilane or halosiloxane with a carboxylic acid amide in the presence of an acid-binding agent such as pyridine or trialkyl amine. Again a salt by-product is produced which must be disposed of.

Klebe, U.S. Pat. No. 3,488,371, assigned to the same assignee as the present invention, describes linear difunctional silylamides which can be produced by reaction of dihalosilicon compounds with an organic amide in the presence of specific tertiary amines.

Toporcer et al., U.S. Pat. No. 3,776,933, teaches the preparation of amidosilanes by mixing a sodium salt of an amide with a chlorosilane in an inert organic solvent, filtering the by-product sodium chloride, and thereafter removing the organic solvent by distillation to obtain the product amidosilane.

Mitchell et al., U.S. Pat. No. 4,252,977, assigned to the same assignee as the present invention, provide a process for forming an acetamide compound of the formula

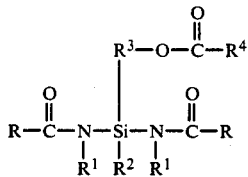

where R, $R^1$, $R^2$ and $R^4$ are monovalent hydrocarbon radicals and $R^3$ is a divalent hydrocarbon radical, comprising
(1) reacting a silane of the formula

where R is as previously defined and X is a halogen with a compound of the formula

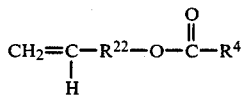

in the presence of a platinum catalyst, where $R^{22}$ is a divalent hydrocarbon radical and $R^4$ is as previously defined, to form an intermediate, and
(2) reacting the intermediate with an amide of the formula

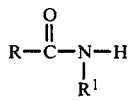

to produce the desired product.

Each of the foregoing references suffer from a disadvantage such as salt or base (e.g. amine) by-product is formed. It has now been discovered that amidosilanes and amidosiloxanes can be prepared by reacting an organic amide having an active hydrogen atom with an Si—H containing compound in the presence of a precious metal containing catalyst, yielding hydrogen gas as the reaction by-product.

SUMMARY OF THE INVENTION

There is provided a process for preparing amidosilanes and amidosiloxanes comprising reacting:
(a) an Si—H containing compound and
(b) an organic amide in the presence of
(c) a precious metal containing catalyst.

Preferably, the reaction is carried out by heating the reactants in a suitable solvent under a nitrogen blanket so as to protect the product from moisture and to dilute the hydrogen gas generated by the reaction.

Compositions prepared in accordance with the present invention are particularly useful as coupling agents and crosslinking agents in silicone room temperature vulcanizable compositions.

DESCRIPTION OF THE INVENTION

In accordance with the present invention there is provided a process for preparing amidosilanes and amidosiloxanes comprising reacting:
(a) an Si—H containing compound and
(b) an organic amide in the presence of
(c) a precious metal containing catalyst.

Generally, suitable Si—H containing compounds are silanes having the general formula $$H_a SiR_{4-a} \quad (I)$$

where R is an organic radical or an organosiloxy radical, preferably a substituted or unsubstituted hydrocarbon radical, an alkoxy radical, or an aryloxy radical, and most preferably a lower alkyl radical, and a is an integer equal to 2, 3 or 4; or polysiloxanes having the general formula $$R_b H_c SiO_{\frac{(4-b-c)}{2}} \quad (II)$$

where R is an organic radical, preferably a hydrocarbon radical, and most preferably a lower alkyl radical, b has a value ranging from 0 to 3, inclusive; c has a value ranging from about 0.005 to 2.0, inclusive; the sum of b and c equals 0.8 to 3.0, inclusive; and the viscosity ranges from about 10 centipoise to about 5000 centipoise at 25° C.

Suitable silanes within the scopes of Formula I are, for example, hexylsilane, phenylsilane, methylhexylsilane, propylsilane, 3,3,3-trifluoropropylsilane, trimethoxysilane, triethoxysilane, diethylsilane, dipropylsilane, diethoxysilane, methylmethoxysilane, phenylmethylsilane, diphenylsilane, and phenylmethoxysilane.

As can be appreciated from the foregoing illustrative examples, in general, silanes used in practicing the present invention can include any substituents which are less reactive than an amide moiety. Such silanes are well known in the art or can be easily ascertained by the artisan without undue experimentation. Of course, mixtures of any suitable silanes can be employed in the practice of the invention.

Organohydrogensiloxanes of Formula II which can be used in practicing the present invention may be resinous, cyclic, substantially linear, or a mixture thereof. There may also be used a mixture of silanes of Formula I and hydrogensiloxanes of Formula II. Organohydrogensiloxanes are also well known in the art, for example, as described in U.S. Pat. Nos. 3,344,111 and 3,436,366, both of which are incorporated by reference into the present disclosure.

When Si—H containing compounds contain only two hydrogen atoms, the amidosilanes and amidosiloxanes prepared in accordance with the present invention are useful as chain-extending materials. If there are present three or more hydrogen atoms the resultant amidosilanes and amidosiloxanes are useful as crosslinking agents.

Organic amides used in the present invention must contain at least one reactive hydrogen atom. Preferably, the organic amides are carboxylic acid amides having the general formula

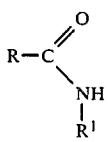

where R is an organic radical, preferably a hydrocarbon radical, and most preferably a lower alkyl radical, and $R^1$ is hydrogen or an R radical.

Also included within the scope of the organic amides of the present invention are lactams (e.g. cyclic amides) of the general formula

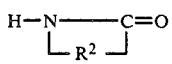

wherein $R^2$ is an alkylene radical; oxindoles of the formula

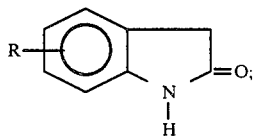

phthalimidines of the formula

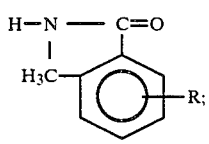

phthalimides of the formula

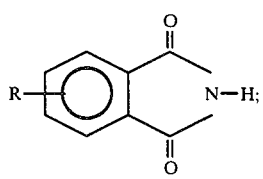

where R is hydrogen or substituted or a unsubstituted hydrocarbon radical.

Other suitable organic amides for use in practicing the present invention will be obvious to those skilled in the art or they can easily be ascertained without undue experimentation.

It is also contemplated that mixtures of organic amides can be utilized in practicing the process of the present invention.

Preferably, the organic amide is present in at least a stoichiometric amount, and more preferably in order to insure that substantially all of the Si—H reacts with the organic amide an excess of organic amide should be employed.

The precious metal containing catalyst can be any catalyst generally employed by those skilled in the art as a hydrosilation catalyst. Preferably, such catalysts are based on platinum metal, but they may be based on other precious metals such as rhodium, ruthenium, palladium, osmium and iridium. Such catalyst can be a precious metal deposited on a charcoal carrier or it can be any of the well known precious metal complexes, for example, as described in the above-mentioned patents describing platinum catalysts.

The precious metal containing catalyst must be present in an amount effective to promote reaction between the Si—H containing compound and the organic amide. Generally, an effective amount of catalyst is from about 10 ppm to about 500 ppm (as weight of metal atoms), and preferably is from about 10 to about 150 ppm catalyst (as weight of metal atoms).

The process of the present invention can be illustrated by the following reaction equation:

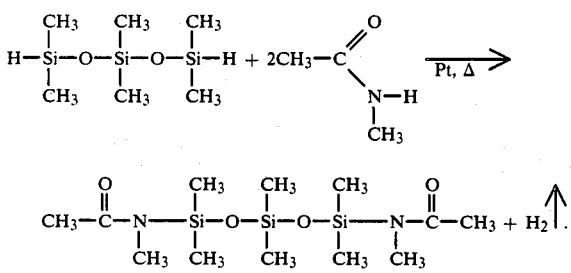

Reaction is preferably carried out in an inert solvent such as benzene, toluene, xylene, N,N-dimethylformamide, N-methyl pyrrolidinone, dimethoxyethyl ether, chlorobenzene, chloroalkanes such as carbon tetrachloride, chloroform, methylene chloride, trichloroethylene, and the like, by heating a mixture of the reactants and catalyst at reflux until substantially all of the silicon-bonded hydrogen atoms have reacted with the organic amide. Analysis of the reaction mass for Si—H by infrared spectroscopy is a convenient means for determining when the reaction has reached completion.

Preferably, the reaction mass is refluxed at a temperature of from about 115° C. to about 135° C. for a period of from about 25 hours to about 125hours. Low boiling solvents require that the reaction be run under pressure and the reaction mixture must be periodically vented to release accumulated hydrogen gas by-product. Desirably, a nitrogen blanket is maintained over the system in order to protect the amidosilane or amidosiloxane from moisture and to dilute the hydrogen gas evolving from the system. The final product can be isolated by vacuum removal of the solvent followed by cooling and filtering.

In order to better enable the artisan to practice the present invention the following examples are provided by way of illustration and not by way of limitation. All parts and percentages are by weight unless otherwise noted.

EXAMPLES

EXAMPLE 1

To a 12 liter flask equipped with a dropping funnel, a thermometer, a mechanical stirrer and a dry ice condenser was added 7 liters of water and 2789 grams (33.2 moles) of sodium bicarbonate. To the dropping funnel was added a mixture of 1032 grams (8 moles) of dimethyldichlorosilane and 1504 grams (16 moles) of dimethylchlorosilane. The mixture in the dropping funnel was added dropwise to the aqueous sodium bicarbonate solution over a period of 10 hours. At the end of the addition the layers were allowed to separate and the upper layer was collected while the lower layer was discarded. The upper product layer was dried over anhydrous magnesium sulfate and filtered. The filtrate was analyzed by gas chromatography for percent composition and for percent Si—H. The analysis showed 0.93% Si—H (0.96% theoretical). Gas chromatography also showed the hydrolyzate to have the following composition: M'M' (7%), M'DM' (70%), M'D$_2$M' (20%) and M'D$_3$M' (2%), where M' is Me$_2$HSiO$_{0.5}$ and D is Me$_2$SiO. The yield of product was 1432 grams (86% theoretical). The resulting hydrolyzate can be purified by distillation to yield greater than 90% pure 1,1,3,3,5,5- hexamethyltrisiloxane.

EXAMPLE 2

To a 1000 ml 3-necked flask was added 208.5 grams (1 mole) purified 1,1,3,3,5,5-hexamethyltrisiloxane prepared in Example 1, 153.3 grams (2.1 moles) of N-methylacetamide, 173.2 grams of toluene and about 120 ppm of platinum containing catalyst (as Pt) prepared in accordance with the teaching of U.S. Pat. No. 3,220,970 to Lamoreaux (hereinafter Lamoreaux catalyst). To the flask was attached a mechanical stirrer, a thermometer and a reflux condenser. The reaction mixture was heated at 100° C. for 20 hours and thereafter heated at 130° C. for 24 hours. At the end of the 44 hour period, analysis by infrared spectroscopy showed no Si—H present in the reaction mixture. The solvent was removed by distillation and the residue filtered through Celite R to give 317.5 grams (90.6% theoretical) of 1,5-bits (N-methylacetamido)-1,1,3,3,5,5-hexamethyltrisiloxane.

EXAMPLE 3

To a 5 liter, 3-necked flask equipped with a mechanical stirrer, a condenser and a thermometer was added 1087 grams (5 moles) of the hydrolyzate prepared in Example 1, 803 grams (11 moles) of N-methyl acetamide, 828 grams of toluene and 125 ppm of Lamoreaux catalyst (as Pt). The mixture was heated at 125°-133° C. for 115 hours whereupon infrared analysis showed the Si—H to be completely consumed. The reaction mixture was distilled to remove toluene and the residue cooled and filtered to isolate 1760 grams (94% theoretical) of an α,ω-bis-amidosiloxane mixture of: M'M' (7%), M'DM' (70%), M'D$_2$M' (20%) and M'D$_3$M' (2%), where M' is $$(CH_3-\underset{\underset{O}{\|}}{C}-\underset{\underset{CH_3}{|}}{N})$$

(Me)$_2$ SiO$_{0.5}$ and D is Me$_2$ SiO.

EXAMPLE 4

To a 5 liter, jacketed, 3-necked flask with a bottom outlet was added 3 liters of water and 1571 grams (18.7 moles) of sodium bicarbonate. Attached to the flask were a mechanical stirrer, a thermometer, a dropping funnel and a reflux condenser. To the dropping funnel was added a blend of 447 grams (3.0 moles) of methyltrichlorosilane and 884 grams (9.4 moles) of dimethylchlorosilane. The chlorosilane blend was added to the rapidly stirred bicarbonate solution over a period of eight hours. At the end of the addition the mixture was vigorously stirred for 30 minutes, then the layers were separated. The bottom layer was discarded while the upper layer was dried over anhydrous magnesium sulfate and filtered. The yield was 680 grams (85% theoretical) of methyl tris(dimethylsiloxy)silane. Analysis of the hydrolyzate showed that it had the following composition: M'M' (9.3%), TM'$_3$ (66.4%), T$_2$M'$_4$ (15.2%) and T$_2$M'$_5$ (1.8%), where T is MeSiO$_{1.5}$ and M' is Me$_2$SiO$_{0.5}$.

EXAMPLE 5

To a 1000 ml 3-necked flask was added 268 grams (1.0 mole) of the hydrolyzate prepared in Example 4, 241 grams (3.3 moles) of N-methylacetamide, 173 grams of toluene and 150 ppm lamoreaux catalyst (as Pt). The mixture was heated at 128°–130° C. for 96 hours. After the heating period infrared spectroscopy showed that substantially all of the Si—H was consumed. The reaction mixture was stripped on a rotary evaporator under vacuum (95° C./25 mm) to provide 465 grams (92% theoretical) of methyl tris(N-methylacetamidodimethylsiloxy)silane.

EXAMPLE 6

The amidosiloxane material obtained in Examples 2 and 3 were shown to be useful as coupling agents by mixing the purified amidosiloxane and the amidosiloxane hydrolyzate, respectively, with a 20,000 molecular weight silanol endstopped polydimethylsiloxane having approximately 0.09% silanol. The amounts chosen were such that there would be about a 1:1 ratio of coupling agent to polymer. When the materials were mixed and set aside for one hour the viscosity increased from 3300 centipoise to over one million centipoise at 25° C. As evidence that substantial crosslinking did not occur, the resulting high molecular weight polymer could be completely dissolved in toluene.

EXAMPLE 7

The amidosilane prepared in Example 5 was shown to be useful as a crosslinking agent by mixing 100 grams of silanol endstopped polydimethylsiloxane having a viscosity of 3400 centipoise at 25° C. with 3 grams of the trifunctional amidosilane hydrolyzate. After thorough mixing the mixture was set aside for 20 minutes. At such time the material was inspected and found to be tack-free. The material had completely cured to an elastomer in two hours.

I claim:

1. A process for preparing amidosilanes and amidosiloxanes comprising reacting:
   (a) an Si—H containing compound and
   (b) an organic amide in the presence of
   (c) a precious metal containing catalyst.

2. A process as in claim 1, wherein the Si—H containing compound is a silane having the general formula $$H_a Si R_{4-a}$$

where R is an organic radical or an organosiloxy radical and a is an integer equal to 2, 3 or 4.

3. A process as in claim 2, wherein R is an organosiloxy radical.

4. A process as in claim 3, wherein the Si—H containing compound comprises methyl tris(N-methylacetamidodimethylsiloxy)silane or a hydrolyzate containing methyl tris(N-methylacetamidodimethylsiloxy)silane.

5. A process as in claim 1, wherein the Si—H containing compound comprises a polysiloxane having the general formula $$R_b H_c SiO_{\frac{(4-a-b)}{2}}$$

where R is an organic radical, b has a value ranging from 0 to 3, inclusive, c has a value ranging from about 0.005 to 2.0, inclusive, the sum of b and c equals 0.8 to 3.0, inclusive, and the viscosity ranges from about 10 centipoise to about 5000 centipoise at 25° C.

6. A process as in claim 5, wherein the Si—H containing compound comprises 1,1,3,3,5,5-hexamethyltrisiloxane or a hydrolyzate containing 1,1,3,3,5,5-hexamethyltrisiloxane.

7. A process as in claim 1, 2 or 5, wherein the organic amide is a carboxylic acid amide having the general formula $$R-\underset{\underset{R^1}{\underset{|}{N-H}}}{\overset{\overset{O}{\|}}{C}}$$

where R is an organic radical and R$^1$ is hydrogen or an R radical.

8. A process as in claim 7, wherein the carboxylic acid amide is N-methylacetamide.

9. A process as in claim 1, wherein the organic amide is a lactam having the general formula $$H-N\underset{\underline{\phantom{xx}R^2\phantom{xx}}}{\overline{\phantom{xxxxx}}}C=O$$

where R$^2$ is an alkylene radical.

10. A process as in claim 1, wherein the organic amide is phthalimidine or phthalimide.

11. A process as in claims 1, 2, or 5, wherein the precious metal containing catalyst is based on platinum.

12. A process as in claims 1, 2 or 5, wherein the organic amide is present in excess of the Si—H containing compound on a stoichiometric basis.

13. A process as in claims 1, 2 or 5, wherein reaction is effected by heating in a solvent for an amount of time effective for reacting substantially all of the si—H bonds.

14. A process as in claims 1, 2 or 5, wherein reaction is effected by heating at a temperature of from about 115° C. to about 135° C. for a period of from about 25 hours to about 125 hours.

15. A process as in claim 12, further comprising maintaining a nitrogen blanket over the reaction mixture.

* * * * *